(12) United States Patent
Gazzani

(10) Patent No.: US 6,969,391 B1
(45) Date of Patent: Nov. 29, 2005

(54) SEMI-RIGID COMPRESSIVE CLAMP FOR USE IN STERNOTOMY, AND FORCEPS FOR ITS APPLICATION

(76) Inventor: Romolo Igino Gazzani, Piazza Matteotti 8, I- 15069 Serravalle Scrivia, Alessandria (IT)

( * ) Notice: Subject to any disclaimer, the term of this patent is extended or adjusted under 35 U.S.C. 154(b) by 0 days.

(21) Appl. No.: 09/959,104

(22) PCT Filed: Apr. 18, 2000

(86) PCT No.: PCT/EP00/03743

§ 371 (c)(1),
(2), (4) Date: Feb. 11, 2002

(87) PCT Pub. No.: WO00/64366

PCT Pub. Date: Nov. 2, 2000

(30) Foreign Application Priority Data

Apr. 21, 1999 (IT) ................................ MI99A0827

(51) Int. Cl.[7] ............................................. A61B 17/58
(52) U.S. Cl. ......................... 606/75; 606/72; 606/151
(58) Field of Search ................................ 606/75, 60, 61, 606/62, 63, 64, 72, 74, 151

(56) References Cited

U.S. PATENT DOCUMENTS

| 2,684,070 | A |   | 7/1954  | Kelsey |        |
|-----------|---|---|---------|--------|--------|
| 4,217,902 | A |   | 8/1980  | March  |        |
| 5,246,443 | A |   | 9/1993  | Mai    |        |
| 5,853,414 | A | * | 12/1998 | Groiso | 606/75 |

FOREIGN PATENT DOCUMENTS

| DE | 42 10 801 | 11/1992 |
| EP | 0 386 361 | 9/1990  |
| EP | 0 743 045 | 11/1996 |
| EP | 0 826 340 | 3/1998  |
| FR | 2 718 634 | 10/1995 |

* cited by examiner

Primary Examiner—Pedro Philogene
Assistant Examiner—Candice C. Stokes
(74) Attorney, Agent, or Firm—Hedman & Costigan, P.C.

(57) ABSTRACT

A clamp designed for use in the heart-surgery field for osteosynthesis following on sternotomy has a roughly C-shaped configuration with a core (11) terminating at opposite ends with hooks (12) set opposite to one another. In the centre, the said core (11) extends vertically according to a plane which is substantially perpendicular to the one on which the end hooks (12) lie, with a loop (13) which is elastically compliant. The said clamp is made of a so-called "shape-memory" metallic alloy, i.e., an alloy which is malleable at a low temperature and which re-acquires its original form at body temperature, exerting a semi-rigid compression on the ends or edges of the bones requiring synthesis.

7 Claims, 3 Drawing Sheets

SEMI-RIGID COMPRESSIVE CLAMP FOR USE IN STERNOTOMY, AND FORCEPS FOR ITS APPLICATION

The present application claims priority to Italian Patent Application No. MI 99A000827, filed Apr. 21, 1999.

BACKGROUND OF THE INVENTION

The present invention refers to a semi-rigid compressive clamp designed for use in the heart-surgery field for osteosynthesis following on sternotomy. The invention moreover refers to a forceps for the application of said clamp.

As is well known to those skilled in the sector, at present one of the systems most widely used for osteosynthesis following on sternotomy involves the use of steel wires, which are made to pass at the rear of the sternum and are tied at the front. However, the use of steel wires gives rise to a number of serious problems as described below. Following upon mobilization of the patient after sternotomy has been carried out, it frequently happens that the steel wires are not able to guarantee optimal osteosynthesis. This is due to the fact that muscular tension during dilation of the thoracic cage (even simply on account of respiratory movements) causes a slight diastasis of the sternal segments, which the steel wire is unable to correct since it is not elastic. There thus remains a certain laxity of the osteosynthesis.

The looseness of grip of the steel wire, which occurs following upon mobilization, above all in patients who are at risk, may cause displacement of the closing knot. The knot itself in these cases causes decubitus of the soft tissue overlying the sternum.

Furthermore, the use of steel wires generally causes a considerable lysis of the bone on the sternal margin.

Another drawback is due to the fact that the point of tying of the steel wires at the front of the sternum may remain slightly raised with respect to the plane of the bone.

In addition, the steel wires for sternal synthesis must be removed before any instrumental investigations, such as x-rays or CAT imaging, are carried out in so far as the wires prevent visualization of the underlying structures.

SUMMARY OF THE INVENTION

The general purpose of the present invention is to overcome the above-mentioned drawbacks of the known art, which, in the field of heart surgery, for osteosynthesis following on sternotomy envisages the use of steel wires, which are made to pass behind the sternum and then are tied in front.

This purpose is achieved by the use of a semi-rigid compressive clamp having the characteristics described in the attached main claim and in the subordinate claims.

Another purpose of the invention is to make a clamp that is particularly suited to the application of the said clam position.

BRIEF DESCRIPTION OF THE DRAWINGS

The structural and functional characteristics of the invention and its advantages with respect to the known art will emerge as clearly understandable from an examination of the following description which refers to the attached drawings showing an example of practical embodiment of the present invention. In the drawings.

DETAILED DESCRIPTION OF THE INVENTION

Figure 1:
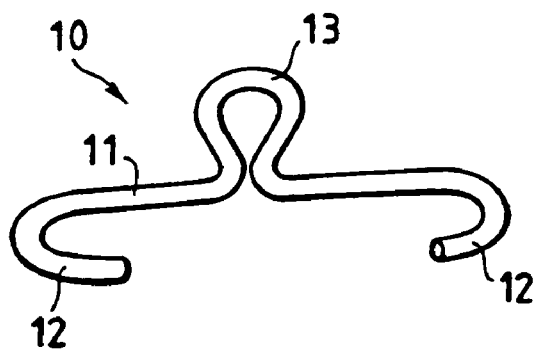
FIG. 1 is a perspective view illustrating a clamp made according to the present invention.

In the drawings, an example of clamp made according to the principles of the present invention is indicated, as a whole, by 10, and may, for example, be advantageously made using the alloy known commercially by the registered trade-mark "NITINOL".

Components made of NITINOL have the characteristic of being malleable at a low temperature (from 0° C. to 5° C.) and of re-acquiring their initial shape at body temperature (37° C.), exerting a semi-rigid compression on the ends or edges of the bones requiring synthesis.

These components are commonly called "shape memory" components. The "shape memory" effect lies in the capacity of the alloy, when subjected to heating, to recover the plastic deformation to which it can be subjected in low-temperature conditions.

The above phenomenon occurs on account of the transformation of the crystalline structures caused by a slight, reversible, movement of flow of each individual atom (martensitic transformation).

The amount of force that is developed in the phase of recovery of shape depends upon factors determined by the constructional peculiarities of the product; namely:

the dimensions of the implant;
the parameters of the semifinished product from which the implant is produced; and
the shape of the cortical spring.

As far as temperatures are concerned, implants made of NITINOL:

are malleable at manipulation temperatures (Mf);
start the memory action at the start temperatures (AS); and
finally return to their original shape at finish temperatures (Af).

Figure 2:
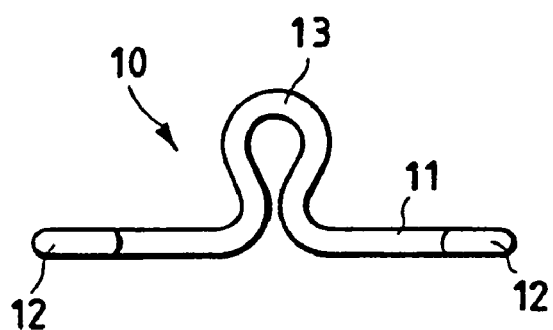
FIG. 2 is a front elevation of the clamp of FIG. 1.
Figure 3:
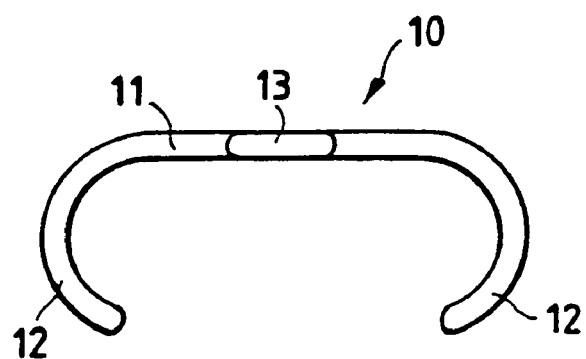
FIG. 3 is a plan view of the clamp of FIGS. 1 and 2.

As may be clearly seen, the sternal clamp 10 illustrated in FIGS. 1–3 of the drawings has a roughly C-shaped configuration, with a core 11 terminating at opposite ends with hooks 12 set opposite to one another.

At the centre, the core 11 extends vertically according to a plane which is perpendicular to the one on which the end hooks 12 lie, with a loop 13 (cortical spring) which is elastically compliant. Using a clamp made of NITINOL, having the configuration described above with reference to FIGS. 1–3 of the drawings, it is possible to position the ends 12 of the C-shaped part 11 in the intercostal spaces S, as represented schematically in FIGS. 4 and 5, after the loop 13 has been opened (divaricated) at a low temperature (from 0° C. to 5° C.).

Figure 4:
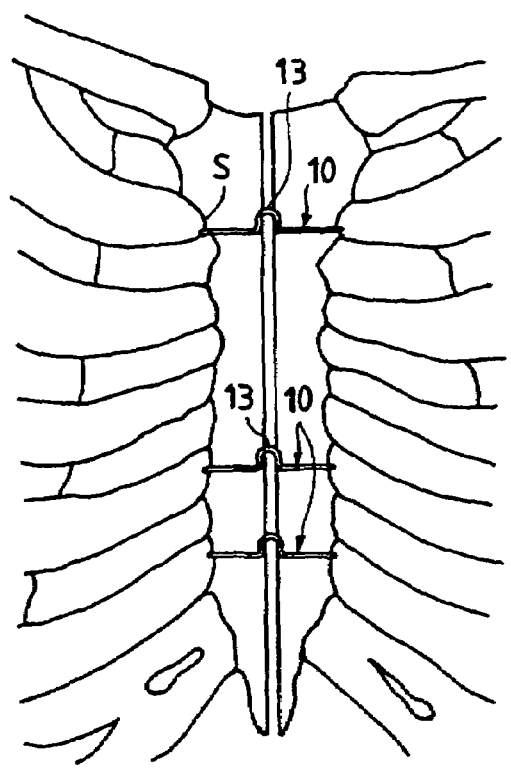
FIG. 4 is schematic view illustrating a plurality of clamps according to the invention, applied for osteosynthesis following on sternotomy, in the open condition.
Figure 5:
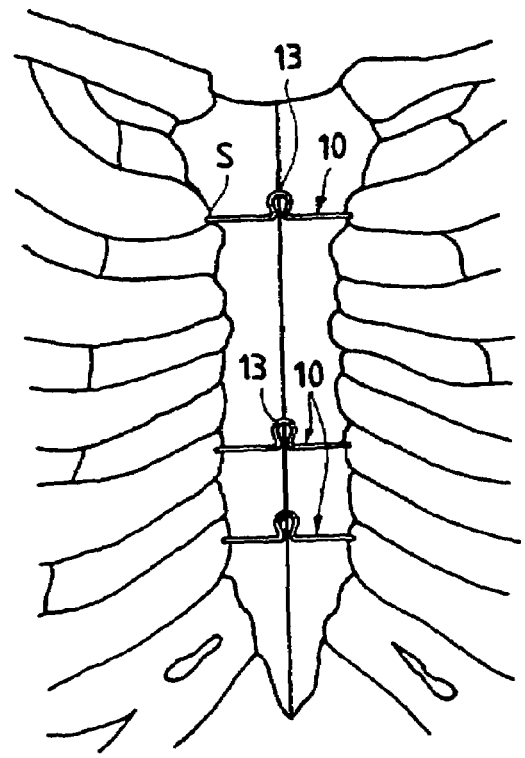
FIG. 5 is a view similar to FIG. 4, but illustrating the clamps in the closed condition.

Next, it suffices merely to irrigate all the clamps 10 positioned as shown in FIG. 4 in the open condition) with physiological solution at body temperature for each clamp 10 to re-close by re-acquiring its original shape (see FIGS. 1–3), so gripping the sternum firmly (FIG. 5).

More precisely, the procedure of application of the clamps according to the invention is described below.

Each clamp is sterilized by putting it in a container that can undergo autoclaving.

The autoclaved container is cooled to a temperature of generally between 0° C. and 5° C. It is, in fact, advisable to expand (i.e., divaricate) the clamp cooled to a temperature of lower than 5° C. to achieve the dimension suitable for its insertion into position, paying particular attention not to modify the curvature of the hooks 12 of the clamp itself so as not to alter the correct anchorage for primary fixation.

The reduction of the sternal osteotomy is blocked using a "BACKHAUS" forceps.

In the intercostal spaces, access paths of adequate dimensions are created for insertion of the terminal hooks 12 of each clamp, as close as possible to the sternum, passing through the anterior and posterior intercostal ligaments. Using a gauge, the horizontal dimensions of the sternum are identified at the level of each individual intercostal space chosen for positioning the clamp.

From among the cooled clamps available, the ones compatible with the dimensions of the sternum as previously identified are used, bearing in mind that the dimensions of the clamp must be smaller by approximately 7–8 mm.

The clamp is now introduced, orienting the cortical spring (elastic loop 13) upwards. The clamp thus positioned resumes its original shape at body temperature, thus firmly gripping the sternum, as shown in FIG. 5.

In this way, the synthesis of the sternum takes place without the latter being surrounded by steel wires—as in the known art—, so preserving the structures of the mediastinum.

The advantages of a semi-rigid compressive sternal clamp for use in sternotomy, such as the one described above with reference to FIGS. 1–5 of the drawings may be summarized as below.

Any laxity of the osteosynthesis, which is always present in those cases where osteosynthesis following on sternotomy is carried out using steel wires, is prevented. In fact, the problem of laxity cannot arise when NITINOL clamps according to the present invention are used, since, owing to the superelasticity of the material, these clamps always maintain their elastic compression.

Mobilization of the patient is thus facilitated and may be envisaged at an early stage without this being detrimental to synthesis of the bone, as instead occurs when steel wires are used.

In addition, the characteristic of the material is such as to cause a markedly lower degree of lysis of the bone on the sternal margin, as compared to the lysis caused by steel wires.

Furthermore, reduction of osteolysis proves extremely useful in operations on patients who are at risk because they are affected by other illnesses (osteoporosis, diabetes, etc.) in which the bone has a lower density.

The use of sternal clamps according to the present invention is particularly indicated in re-implants in the case of post-operative dehiscence—especially if this occurs late—in which isolation of the adhesions underlying the sternum, which is necessary for closing with steel wires, may jeopardize the internal mammary artery on both sides. In these cases, approximation of the sternum, without this being surrounded by steel wires, may be advisable, as well as being far more convenient.

When NITINOL clamps according to the present invention are used, considering the geometry of the product, decubitus of the soft tissue overlying the sternum, which is caused instead by displacement of the closing knot in the case where steel wires are used, cannot arise.

In addition, the characteristics of "NITINOL" are such that this alloy does not interfere with ionizing radiation, and hence instrumental examinations (x-rays or CAT imaging) may be carried out without prior removal of the bone-synthesis clamps.

NITINOL does not present elastic fatigue, is non-toxic, and has a higher biocompatibility than do other implants made of special steel.

Figure 6:
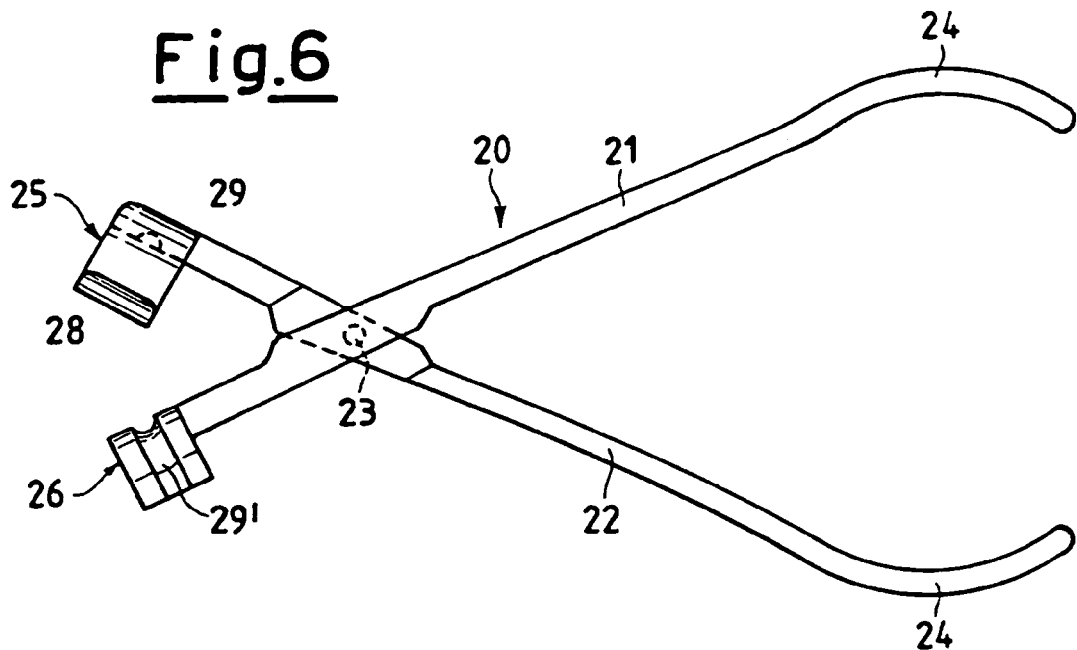
FIG. 6 is a plan view illustrating forceps for the application of the clamp of FIGS. 1–5, in the open condition.
Figure 7:
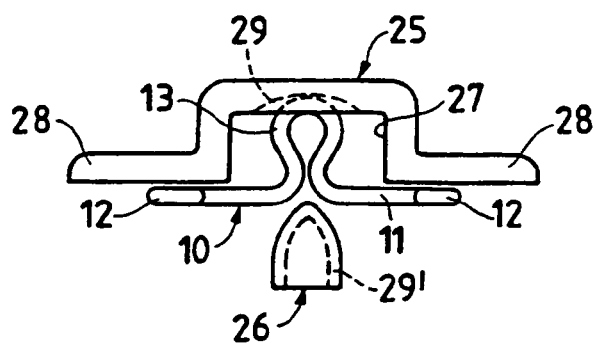
FIG. 7 is a front elevation of the forceps of FIG. 6, with the clamp inserted between the jaws during closing.
Figure 8:
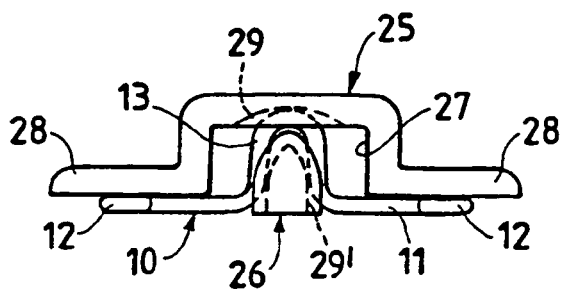
FIG. 8 is a view similar to FIG. 7, illustrating the forceps closed on the clamp in the condition of divarication of the loop, i.e., of application of the clamp in place.

Finally, the sternal clamps according to the present invention may also be used in paediatric surgery. For such an application, both the dimensions and the compressive force are adapted in proportion to the smaller resistance of the bone. Also in this case, removal of the means of synthesis is not required since, with the growth of the sternum, the clamps are englobed in the bone. FIGS. 6–8 of the drawings illustrate an example of forceps which can be used for the divarication of the loop 13, which can, in this way, be applied in situ, as shown in FIG. 4.

The said forceps is indicated as a whole by the reference number 20, and consists of two levers 21, 22 pivoted together at an intermediate point 23.

Each of the said levers 21, 22 terminates, at one end, with a grip which can be of any shape, for example, it can have the shape of an arched section 24, whilst at the opposite end the levers are equipped with respective opposed jaws 25, 26.

The jaw 25 has a fret-shaped cross section identifying a C-shaped seat 27 from which opposite flanges 28 extend, the seat being designed to house the clamp 10.

More precisely, the seat 27 has a recess or "cradle" 29 for receiving the loop 13, whilst the core 11 of the clamp 10 bears upon the flanges 28, as illustrated in FIG. 7.

The jaw 26 has, instead, a wedge-shaped cross section that has a groove as indicated by 29'. Operation of the forceps according to the invention is evident from FIGS. 6–8 and is briefly described in what follows.

The clamp 10 is positioned between the jaws 25, 26 (which are partially closed), as shown in FIG. 7. Next, the forceps is closed completely, as shown in FIG. 8, so as to cause the wedge-shaped jaw 26 to insert inside the loop 13, which is thus divaricated.

In this condition, the clamp 10 may be applied in situ, as shown in FIG. 4.

In this way, the purposes mentioned in the preamble of the description are achieved. The scope of the present invention is defined by the ensuing claims.

What is claimed is:

1. A clamp for osteosynthesis following a sternotomy said clamp having a C-shaped configuration, two opposite ends and a core (11) which is terminated by said opposite ends, said opposite ends having hooks (12), including terminal ends said core (11) consisting of only a single loop (13) which is elastically compliant and is centered on said C-shaped clamp, said clamp being made of a memory retaining metallic alloy, wherein said clamp is designed for use in the field of heart-surgery for osteosynthesis following a sternotomy, said loop (13) being extended vertically to a first plane which is substantially perpendicular to a second plane in which all of said end hooks (12) lie, said end hooks being adapted to exert a force against each other when placed in position over a sternotomy wherein said clamp before application is maintained in a malleable condition at a low temperature, and after application re-acquires said clamp's original form as the temperature of said clamp increases towards body temperature, thereby exerting a semi rigid compression on ends or edges of bones requiring synthesis.

2. A clamp according to claim 1, wherein said shape-memory metallic alloy is a nickel and titanium alloy that is malleable at temperature from about 0° C. to about 5° C. and reacquires initial shape at about 37° C.

3. A medical device comprising a combination of forceps and said clamp (10) as defined in claim 1, wherein said forceps comprise two levers (23, 22) hinged together at an intermediate point (23), said levers being provided with respective opposed jaws (25, 26) between which said clamp (10) may be inserted, said jaws (25, 26) being provided with means for divaricating said loop (13) of said clamp (10) in the closing position of said forceps.

4. The medical device according to claim 3, wherein said forceps further comprise said divaricating means consisting of a seat for said clamp (10) in said jaw (25) and of a wedge-shaped section in said jaw (26) which is designed to wedge into said loop (13) so as to divaricate said clamp (10) when said forceps are closed.

5. The medical device according to claim 4, wherein said forceps further comprise said jaw (25) comprising a fret-shaped cross section defining a C-shaped seat (27) from which opposite flanges (28) extend, said seat being designed to house said clamp (10) with said core (13) bearing upon said flanges (28).

6. The medical device according to claim 5, wherein said forceps further comprise said seat (27) comprising a recess or "cradle" (29) for receiving said loop (13), whilst the wedge-shaped section of said jaw (26) has a groove (29') for opening said loop.

7. A method for clamping an osteosynthesis following a sternotomy, said method comprising applying to the edges of a sternotomy a clamp, said clamp having a C-shaped configuration, two opposite ends and a core (11) which is terminated by said opposite ends, said opposite ends having hooks (12), said core (11) comprising a loop (13) which is elastically compliant and is centered on said C-shaped clamp, said clamp being made of a memory retaining metallic alloy, wherein said clamp is designed for use in the field of heart-surgery for osteosynthesis following a sternotomy, said loop (13) being extended vertically to a plane which is substantially perpendicular to a plane in which said end hooks (12) lie, said end hooks (12) having terminal portions which oppose one another, said end hooks being adapted to exert a force against each other when placed in position over a sternotomy, wherein said clamp before application is maintained in a malleable condition at a low temperature, and after application re-acquires said clamp's original form as the temperature of said clamp increases towards body temperature, thereby exerting a semi rigid compression on ends or edges of a sternotomy.

* * * * *